United States Patent
Chin et al.

(10) Patent No.: US 9,623,192 B2
(45) Date of Patent: Apr. 18, 2017

(54) SAFETY SHIELD SYSTEM FOR A SINGLE USE FLEXIBLE-TYPE COMPRESSION SYRINGE, AND INJECTION DEVICE

(75) Inventors: Sin Fong Chin, Singapore (SG); Jon Moh Yaohan, Singapore (SG); Trong Yee Sim, Kulai (MY)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1367 days.

(21) Appl. No.: 13/354,818

(22) Filed: Jan. 20, 2012
(Under 37 CFR 1.47)

(65) Prior Publication Data
US 2012/0238962 A1    Sep. 20, 2012

Related U.S. Application Data

(63) Continuation of application No. 12/526,201, filed as application No. PCT/US2007/003145 on Feb. 7, 2007, now abandoned.

(51) Int. Cl.
*A61M 5/32* (2006.01)
*A61M 5/28* (2006.01)

(52) U.S. Cl.
CPC ........ *A61M 5/3216* (2013.01); *A61M 5/3269* (2013.01); *A61M 5/282* (2013.01);
(Continued)

(58) Field of Classification Search
CPC .......... A61M 2005/325; A61M 5/3273; A61M 25/0618; A61M 25/0631; A61M 5/3243;
(Continued)

(56) References Cited

U.S. PATENT DOCUMENTS 2,617,359 A * 11/1952 Horn Van ..................... 102/512
4,573,976 A    3/1986 Sampson et al.
(Continued)

FOREIGN PATENT DOCUMENTS

CN    2655924 Y    11/2004
EP    0 708 667 B1    10/2001
(Continued)

OTHER PUBLICATIONS

English Translation of Official Notice of Rejection from the Japanese Patent Office dated Dec. 27, 2011.
(Continued)

*Primary Examiner* — Scott Medway
(74) *Attorney, Agent, or Firm* — The Webb Law Firm

(57) ABSTRACT

A safety shield system (60) for a compression syringe (10) having a compressible reservoir (46), a needle cannula (12) for fluid communication with the reservoir (46) and having a forward tip (16), the safety shield system (60) having at least a holder shield portion (62) designed to be attached to the compression syringe (10), and a movable shield portion (64), designed to be movable relative to the compression syringe (10) from a first position wherein the tip (16) is exposed, to a second position wherein the movable shield portion (64) covers the tip (16). The holder shield portion (62) and movable shield portion (64) being provided with retainer (51, 52, 70) arranged to cooperate in the first position to prevent the movable shield portion (64) from moving toward its second position.

21 Claims, 8 Drawing Sheets

(52) U.S. Cl.
CPC ............ *A61M 5/288* (2013.01); *A61M 5/326* (2013.01); *A61M 5/3219* (2013.01); *A61M 5/3257* (2013.01); *A61M 2005/3247* (2013.01)

(58) Field of Classification Search
CPC ............ A61M 5/3257; A61M 25/0625; A61M 2005/3247; A61M 25/0612; A61M 5/3271; A61M 5/282; A61M 5/2425
See application file for complete search history.

(56) References Cited

U.S. PATENT DOCUMENTS

| | | | | |
|---|---|---|---|---|
| 4,581,021 A * | 4/1986 | Landau | ............... | A61M 5/2425 222/103 |
| 4,850,977 A * | 7/1989 | Bayless | ............... | 604/198 |
| 4,887,998 A * | 12/1989 | Martin et al. | ............... | 604/110 |
| 4,900,311 A * | 2/1990 | Stern et al. | ............... | 604/198 |
| 4,929,237 A * | 5/1990 | Medway | ............... | 604/198 |
| 4,955,866 A | 9/1990 | Corey | | |
| 4,955,871 A | 9/1990 | Thomas | | |
| 4,976,561 A * | 12/1990 | Kageyama | ............... | 401/75 |
| 5,156,599 A * | 10/1992 | Ranford et al. | ............... | 604/198 |
| 5,176,655 A * | 1/1993 | McCormick et al. | ............... | 604/198 |
| 5,254,099 A * | 10/1993 | Kuracina et al. | ............... | 604/198 |
| 5,312,372 A * | 5/1994 | DeHarde | ............... | A61M 5/3269 604/110 |
| 5,344,408 A * | 9/1994 | Partika | ............... | 604/192 |
| 5,348,544 A * | 9/1994 | Sweeney et al. | ............... | 604/192 |
| 5,360,408 A * | 11/1994 | Vaillancourt | ............... | 604/198 |
| 5,411,492 A * | 5/1995 | Sturman et al. | ............... | 604/263 |
| 5,466,223 A * | 11/1995 | Bressler et al. | ............... | 604/110 |
| 5,584,818 A * | 12/1996 | Morrison | ............... | 604/197 |
| 6,056,726 A * | 5/2000 | Isaacson | ............... | 604/164.01 |
| 6,102,896 A * | 8/2000 | Roser | ............... | A61M 5/28 604/124 |
| 6,322,540 B1 * | 11/2001 | Grabis et al. | ............... | 604/198 |
| 6,443,929 B1 * | 9/2002 | Kuracina et al. | ............... | 604/192 |
| 6,808,507 B2 * | 10/2004 | Roser | ............... | A61M 5/282 604/110 |
| 6,979,316 B1 * | 12/2005 | Rubin et al. | ............... | 604/156 |
| 8,486,024 B2 * | 7/2013 | Steube | ............... | 604/164.08 |
| 8,597,257 B2 * | 12/2013 | Modi | ............... | A61M 5/282 604/110 |
| 2003/0014019 A1 | 1/2003 | Saied | | |
| 2003/0028171 A1 | 2/2003 | Deharde et al. | | |
| 2005/0124938 A1 | 6/2005 | Yang | | |
| 2009/0171311 A1 * | 7/2009 | Genosar et al. | ............... | 604/411 |
| 2009/0227956 A1 * | 9/2009 | Emmott et al. | ............... | 604/196 |
| 2013/0245564 A1 * | 9/2013 | Cheng | ............... | 604/195 |

FOREIGN PATENT DOCUMENTS

| | | |
|---|---|---|
| EP | 1346741 | 9/2003 |
| EP | 1410818 | 4/2004 |
| FR | 2796287 | 1/2001 |
| JP | 02046861 | 2/1990 |
| WO | WO/95/02427 | 1/1995 |

OTHER PUBLICATIONS

PCT International Preliminary Report on Patentability (Chapter I of the Patent Cooperation Treaty) and Written Opinion, Aug. 20, 2009.

* cited by examiner

SAFETY SHIELD SYSTEM FOR A SINGLE USE FLEXIBLE-TYPE COMPRESSION SYRINGE, AND INJECTION DEVICE

1. CROSS REFERENCE TO RELATED APPLICATIONS

This application is a continuation of U.S. patent application Ser. No. 12/526,201 now abandoned which was filed with the U.S. Patent and Trademark Office on Aug. 6, 2009 as a national stage of application No. PCT/US07/03145, filed on Feb. 7, 2007, the entire contents of the foregoing are incorporated by reference.

BACKGROUND OF THE INVENTION

2. Field of the Invention

The present invention relates to a safety-shield system for a syringe and, more particularly, for a single use flexible-type compression syringe. The present invention also relates to an injection device with such a safety shield system.

3. Description of the Related Art

A "compression syringe", as used herein means a" syringe which hold medicament in a reservoir defined walls with at least one being compressible and when squeezed by a user's hand, causes the medicament to be expelled out from the reservoir and administered to a patient through a needle cannula connected to the reservoir. Compression syringes are prefilled with a single dose of the medicament which is completely delivered upon compressing the reservoir. Because of their lightweight and compact properties, their ruggedness and low cost, compression syringes are favored in many circumstances.

A known compression syringe assembly is depicted in FIGS. 1 and 2 and is described in U.S. Pat. No. 4,955,871. The compression syringe 10 includes a reservoir 46 which is configured to be rendered unusable upon discharge of a full dose of medicament. To operate the compression syringe 10, a protector cap 30 must be removed to expose a needle cannula 12 connected to the reservoir 46. To avoid contamination from the used compression syringe 10, the needle cannula 12 must be covered after use. For the compression syringe 10 shown in FIGS. 1 and 2, this is accomplished by re-capping the needle cannula 12 with the protector cap 30. However, this task may cause the compression syringe 10 users, such as health care professionals to accidentally stick themselves while replacing the cap 30. Accordingly, there is a need for a safety shield system that can cover an exposed needle cannula tip of a compression syringe after use to prevent exposure to the used needle cannula tip.

SUMMARY OF THE INVENTION

It is an object of the present invention to provide a single use flexible-type compression syringe with a safety shield system having a moveable shield portion which is movable between a retracted first position in which the tip of a needle cannula is exposed, and an extended second position in which a forward tip of the needle cannula is covered.

It is a further object of the present invention to provide a safety shield system that can be activated through normal operation of a compression syringe with which it is assembled to allow a movable shield portion to move from a first retracted position wherein a forward tip of a needle cannula is exposed for administering medicament, to a second extended position wherein the movable shield portion extends over the forward tip of the needle cannula to prevent contact with the used needle cannula forward tip.

It is a further object of the present invention to provide an injection device having such a safety shield system.

These and other objects are addressed by a safety shield system for a single use flexible-type compression syringe having a compressible reservoir, a needle cannula for fluid communication with the reservoir and having a forward tip. The safety shield system comprising at least a holder shield portion designed to be attached to the compression syringe, and a movable shield portion designed to be movable relative to the compression syringe from a first position wherein the tip is exposed, to a second position wherein the movable shield portion covers the tip. The holder shield portion and movable shield portion are provided with retaining means arranged to cooperate in the first position to prevent the movable shield portion from moving toward its second position. The safety shield system is characterized in that part of the retaining means are provided on a deflectable part connected to at least one of the holder shield portion or movable shield portion, the deflectable part being manually deflectable to disengage, when deflected, the retaining means and allow the movable shield portion to be moved toward its second position.

In one embodiment, the movable shield portion is connected with the holder shield portion by a sliding connection allowing the movable shield portion to translate relating to the holder shield portion between the first and second positions.

In another embodiment, one of the holder shield portion and the movable shield portion has respectively at least one guide rail or a sliding part complementary to the guide rail, the guide rail and the sliding part defining the sliding connection.

Advantageously, the movable shield portion is connected with the holder shield portion by a pivoting connection allowing the movable shield portion to pivot relating to the holder shield portion between the first and second positions.

Each of the movable shield portion and holder shield portion preferably comprises at least one abutment surface, one being provided on the deflectable part, the abutment surface being arranged to abut against each other in the first position to, define the retaining means.

In still another embodiment, the movable shield portion and the holder shield portion are connected to each other by at least one frangible rib arranged to break upon compression of the deflectable part and defining the retaining means.

At least part of the deflectable part can be located in order to be in regards to the reservoir when the safety shield system is assembled with a compression syringe in order to be able to, when the deflectable part is manually defected, squeeze the reservoir to expel said product out of the compression syringe.

The sliding connection or the pivoting connection are preferably arranged in order to limit friction between the movable shield portion and holder shield portion, to enable the free displacement of the movable shield portion toward the second position upon orienting the sharp pointed end toward the ground.

In yet another embodiment, the safety shield system comprises a locking means arranged to lock the movable shield portion in the second position.

One of the holder shield portion and movable shield portion advantageously contains at least a first ramped notch and the other contains at least a first flexible; catch arranged to be locked in the first ramped notches when the movable shield portion is in the first position to prevent the movable shield portion from moving from said first position.

In another embodiment, one of the holder shield portion and movable shield portion contains at least a second ramped notch arranged to lock the catch when said movable shield portion is in the second position to prevent the movable shield portion from moving from the second to first ramped notch, the second notch and catch defining part of the locking means.

In a further embodiment, the safety shield system comprises an urging member positioned between the movable shield portion and the holder shield portion, for example a spring, that is used to urge the movable shield toward its second position.

The front portion of the movable shield portion advantageously defines an aperture through which the needle cannula extends when the safety shield system is assembled with a compression syringe and the movable shield portion is in the first position.

In another embodiment, the movable shield portion defines a L shape, the small branch of the L shape comprising the aperture and the long branch of the L shape defining part of the connecting means.

In yet another embodiment, the holder shield portion is provided with at least one gripping surface designed to be hold by the user during operation of the safety shield system and/or of the compression syringe.

In still another embodiment, the front portion of the holder shield portion defines a port designed to receive the needle hub when the safety shield system is assembled with a compression syringe.

The holder shield portion has preferably a U shape, one branch of the U shape defining a gripping surface, the other branch defining at least part of the connecting means, the basis of the U shape being formed by wings extending away from the port in opposite directions to the gripping surface and the connecting means.

The front portion of the holder shield portion is advantageously configured to receive a portion of the basis of the overall "U" shape when the movable shield portion is in the first position.

Each of the first and second ramped notches can consist of a substantially perpendicular back edge relative to the travel direction of the movable shield portion toward its second position, and a curved front wall, the curved front wall of the second one of the ramped notches causing movement of the catch out of the second one of the notches as the catch is moved from the second one of the notches to the first one of the notches.

In another embodiment, said second ramped notches is coupled with at least one stop surface arranged to prevent said catch to move past said second position, said stop surface and catch defining part of said locking means.

The invention also relates to an injection device comprising a compression syringe having a compressible reservoir, a needle cannula for fluid communication, with the reservoir, the needle cannula having a tip, the injection device further comprising a safety shield system as previously described.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
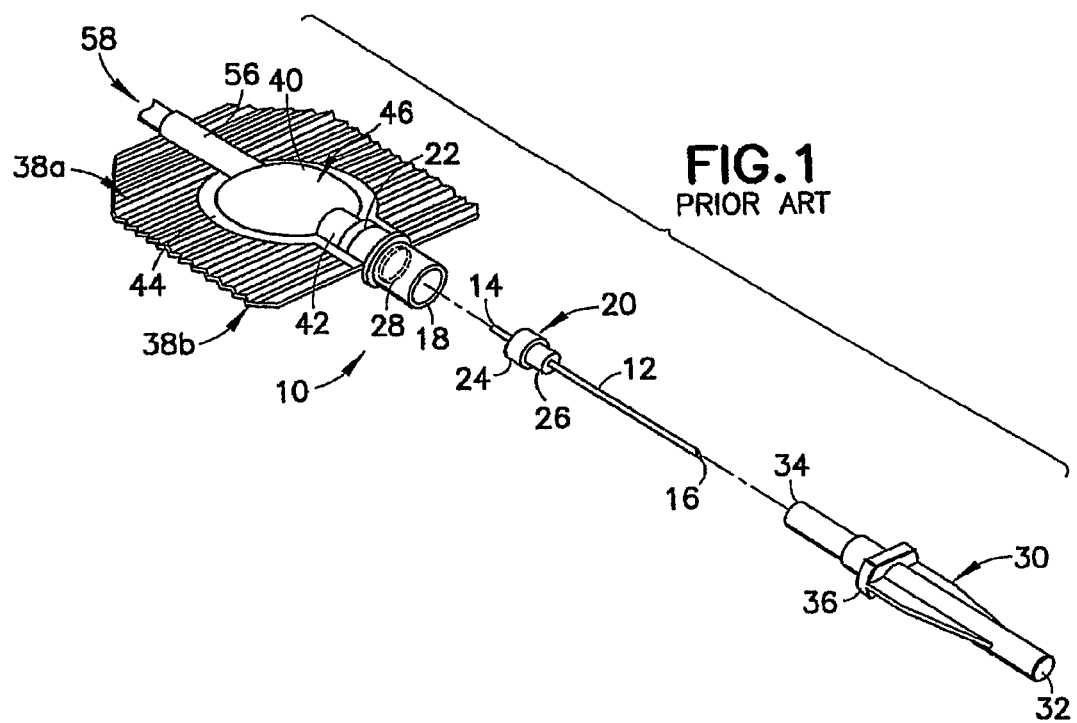
FIG. 1 is a perspective view of a prior art compression syringe assembly in an exploded view.
Figure 2:
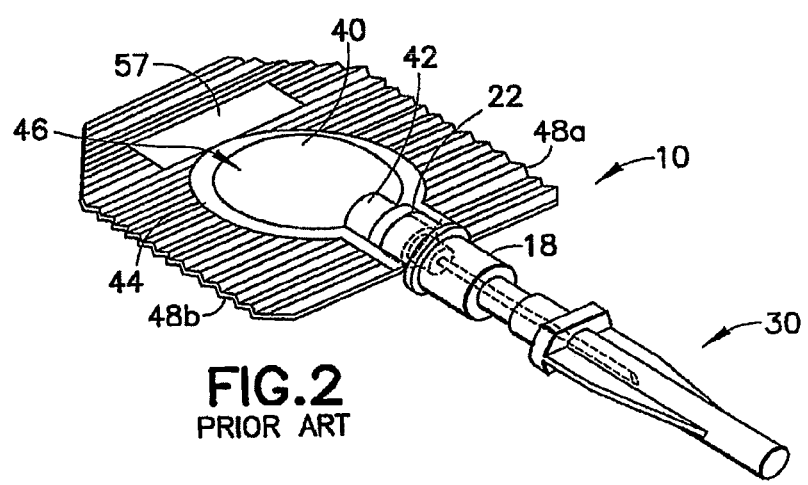
FIG. 2 is a perspective view of the compression syringe assembly of FIG. 1 in an assembled view.

A known single-use flexible-type compression syringe for providing a medicament for injection into a patient is shown in FIGS. 1 and 2 and is represented graphically by the numeral 10. The compression syringe 10, which is the subject of U.S. Pat. No. 4,955,871, the entire content of which is hereby incorporated by reference, includes needle assembly means for injecting the medicament into the patient. The needle assembly means includes a needle cannula 12 that is pointed at both sharp pointed ends 14 and tip 16. The needle assembly means contains hub means fastened to the needle cannula 12. The needle assembly means also includes a tube for holding the needle hub means. The tube has a closed end connected to an injection port, and an open end. Preferably, the tube is provided by a nozzle 18, the hub means is provided by a needle hub 20, and the closed end of the tube is formed by a nozzle membrane 22.

As illustrated in FIGS. 1 and 2, needle cannula 12 passes through needle hub 20. The needle hub 20 is made of polystyrene and is preferably secured to needle cannula 12 using an adhesive, such as an epoxy resin. In this embodiment, nozzle 18 and needle hub 20 are cylindrical in shape. Preferably, needle hub 20 is comprised of a first section 24 of large diameter and a second section 26 of small diameter. The dimensions of large diameter first section 24 and of the internal diameter of nozzle 18 are selected so that needle hub 20 is frictionally held within nozzle 18, but can be moved laterally within nozzle 18 when a force is applied to needle hub 20, as explained below. One of the sharp pointed ends 14 of needle cannula 12 penetrates nozzle membrane 22 when needle hub 20 is moved toward the nozzle membrane 22. The tip 16 of needle cannula 12 is used to administer the medicament, for example intravenously, or intramuscularly through the skin of a patient.

Nozzle 18 also is provided with an internal rib 28 between nozzle membrane 22 and needle hub 20 to prevent sharp pointed end 14 of the needle cannula 12 from piercing the closed end of the tube unless a sufficient force is applied. The dimensions of large diameter first section 24 and of internal rib 28 are selected so that needle hub 20 will not move past rib 28 unless a sufficient force is applied to needle hub 20. This structure reduces the risk of unintentional piercing of nozzle membrane 22.

Means are provided for protecting the needle cannula 12. As shown in FIG. 1, syringe 10 has a protector cap 30 which is a cylinder having a closed end 32 and an open end 34. Protector cap 30 is long enough, together with nozzle 18, to enclose needle cannula 12 without permitting the closed end of the protector cap 30 to come into contact with tip 16 of the needle cannula 12. The open end of the protector cap 30 fits inside the nozzle 18, and preferably the external diameter of the open end is selected so that the protector cap 30 is snugly held in position within nozzle 18. As a result, the needle cannula 12 is kept sterile and is not exposed during storage and shipment of the compression syringe 10. Following the piercing of nozzle membrane 22 by sharp pointed end 14, protector cap 30 is removed to expose needle end 16 for administering an injection.

The means for axially moving the needle cannula 12 within the tube to pierce the closed end of the tube with sharp pointed end 14 of the needle cannula 12 is provided by cooperation of protector cap 30 with needle hub 20. The internal diameter of open end 34 of the protector cap 30 is selected so that the small diameter second section 26 of needle hub 20 fits snugly within the open end 34 of the protector cap 30. The external diameter of open end 34 of the protector cap 30 is selected so that the protector cap 30 can be moved laterally within nozzle 18. This design permits axial movement of needle cannula 12 without angular displacement of the needle cannula 12 as it moves toward and through nozzle membrane 22 at the closed end of nozzle 18.

As shown in FIG. 2, protector cap 30 can be used as a tool in which open end 34 of the protector cap 30 is pushed against the large diameter first section 24 of needle hub 20. In this way, a sufficient force can be safely applied to needle hub 20 to force it past internal rib 28. Protector cap 30 then continues pushing large diameter first section 24 of needle hub 20 until sharp pointed end 14 of needle cannula 12 penetrates nozzle membrane 22. The protector cap 30 is long enough to allow needle hub 20 and needle cannula 12 to be axially moved far enough within nozzle 18 to pierce nozzle membrane 22 with sharp pointed end 14 of the needle cannula 12. The protector cap 30 may also include an external rim 36 which allows a person handling the compression syringe 10 to more easily control the axial movement of needle hub 20 within the nozzle 18 by applying a force to the external rim 36.

The prior art compression syringe 10 of FIGS. 1 and 2 includes reservoir means for storing medicament and for expelling the medicament into the needle assembly means. The reservoir means is formed from a pair of flexible sheets 38a and 38b of thermoplastic material. Each sheet 38a, 38b has an edge 48a, 48b, a central portion 40, an injection neck portion 42, and a peripheral portion 44. Peripheral portion 44 is substantially flat, and the injection neck portion 42 is expanded. The substantially flat peripheral portions 44 of the two sheets 38a, 38b of thermoplastic material are opposite and coextensive to each other and are sealed together face-to-face to form a reservoir 46 inside the central portion 40. The reservoir 46 is filled with medicament via a filling neck portion 56 (see FIG. 1) having a filling port 58 as explained more fully in U.S. Pat. No. 4,955,871. Following the filling step, filling port 58 of the two flexible sheets 38a, 38b are heated sealed together by a specific sealing portion or region 57 (see FIG. 2).

To use the compression syringe 10 of FIGS. 1 and 2, the protector cap 30 is pushed back against the needle hub 20 to cause sharp pointed end 14 of the needle cannula 12 to pierce the nozzle membrane 22, thus placing the needle cannula 12 in communication with the reservoir 46. Thereafter, the protector cap 30 is removed and a patient's skin is pierced with the tip 16 of the needle cannula 12. To administer the medicament, the central portion 40, i.e. the flexible wall defining the reservoir 46, is compressed such as between the thumb and forefinger of the injection device user. After the medicament is administered, the needle cannula 12 is withdrawn from the patient and must be covered to avoid, exposure and possible contamination from the now-exposed needle tip 16. Although the protector cap 30 can be used- to re-cover the needle cannula 12, this technique has drawbacks because the user may accidentally puncture himself/herself as the protector cap 30 is being replaced over the used tip 16.

Accordingly, and with reference to FIGS. 3, 3a to 3d and 4, an improved injection device is shown which includes a compression syringe 10 and a safety shield system 60. The safety shield system 60 is used to cover the exposed tip 16 of needle cannula 12 after an injection is performed, such that a user of the compression syringe 10 will be protected from needle prick injury by the used needle cannula 12. The safety shield system 60 is configured for attachment to the compression syringe 10 of FIGS. 1 and 2. Once the compression syringe 10 is filled with medicament, a sealing portion 57 is formed such as by crimping or melting a portion of the sheets 38a, 38b to seal the medicament in the reservoir 46. As shown, the safety shield system 60 extends from a front of the compression syringe 10 proximate the nozzle 18 along the edges 48a, 48b to the sealing portion 57.

In one embodiment, the safety shield system 60 has two primary components, a holder shield portion 62 and a movable shield portion 64. Both components are mounted to respective edges 48a, 48b of flexible sheets 38a, 38b. In the depicted embodiment the holder shield portion 62 has an overall "U" shape and is provided with a "U" shape cross-section dimensioned to provide a friction fit with edges 48a. Alternatively, the holder shield portion can be directly connected to the compression syringe in any other manner, such as by crimping, molding, adhesive, etc. The holder shield portion 62 provides a gripping surface 63 intended to be grasped by the user for using the injection device. A coupling member 66 is provided to connect the movable shield portion 64 to edges 48b of the flexible sheets 38a, 38b.

In an alternate embodiment, holder 62, a hub brace 74, and coupling member 66 can be integrally formed into a "U" shaped member for securing about the compression syringe 10 such as by friction fit, crimping, molding, adhesive, etc.

In another alternate embodiment, the holder portion 62 can be omitted, in which event a user of the compression syringe 10 can simply hold the injection device by grasping edge 48a.

Figure 10:
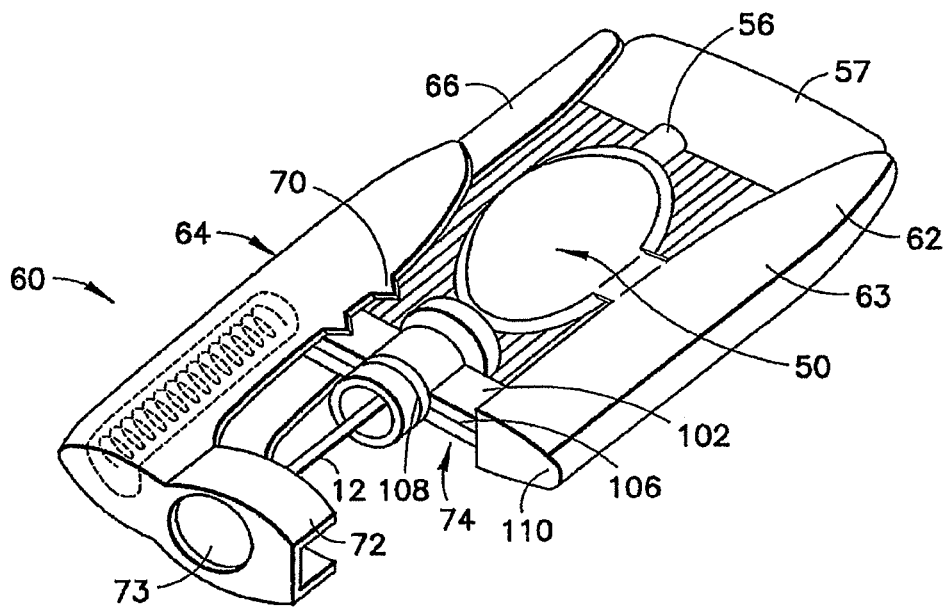
FIG. 10 is a perspective view of the safety shield system of FIG. 8 with the movable shield portion in the second position related to the holder shield portion.
Figure 11:
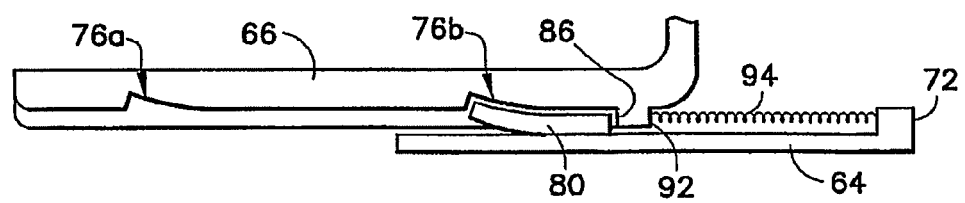
FIG. 11 is a side view illustrating the safety shield system of FIG. 10 with the movable shield portion in the second position related to the holder shield portion.

In the depicted embodiment, the basis of the "U" shaped holder shield portion 62 is positioned at the front end of the compression syringe 10 and includes a curved central portion defining a port 108 through which the nozzle 18 extends as shown in FIG. 10. A pair of wings 102, 104 extends from the central portion along the front edge of the compression syringe 10. Wing 102 defines a slot 106 (see FIG. 10) to provide securement of the holder shield portion 62 to the front edge of the compression syringe 10, such as by friction fit, crimping or adhesive, etc.

As explained more fully below, the movable shield portion 64 is automatically moveable from a retracted first position depicted in FIG. 3 wherein the forward tip 16 of the needle cannula 12 is exposed, to a second extended position shown in FIG. 4 wherein the tip 16 is covered. Movement of the movable shield portion 64 occurs by sliding motion of the movable shield portion 64 along coupling member 66, which functions as a guide rail. One way this is accomplished is by forming the movable shield portion 64 with a "U" shaped cross-section of a dimension slightly wider than the width of the coupling member or guide rail 66 (these terms are used interchangeably herein) to seat about the guide rail 66 such that a groove 67 is formed as shown in FIG. 3a to provide clearance for slidable movement of the movable shield portion 64. Indented legs or hooks 90 are provided on the movable shield portion 64 to radially secure the movable shield portion 64 to the guide rail while allowing for axial movement of the movable shield portion 64 along the length of the guide rail 66.

The moveable shield portion 64 has an overall "L" shape defining a front portion 72 having an aperture 73 therein through which the nozzle 18 and needle cannula 12 extend when the movable shield portion 64 is in the first position. The front portion 72 of the movable shield portion 64 is dimensioned to receive a portion of the hub brace 74 as shown in FIGS. 3 and 4 when the movable shield portion 64 is in the retracted first position.

Figure 5:
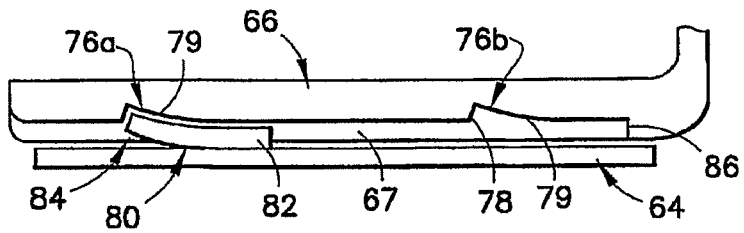
FIG. 5 is a side view illustrating the safety shield system of the invention, with the movable shield portion in the first position related to the holder shield portion.
Figure 6:
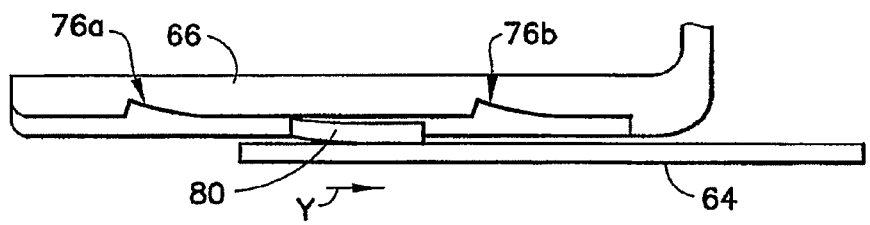
FIG. 6 is a side view illustrating the safety shield system of the invention with the movable shield portion in an intermediate position between the first position and the second position related to the holder shield portion.
Figure 7:
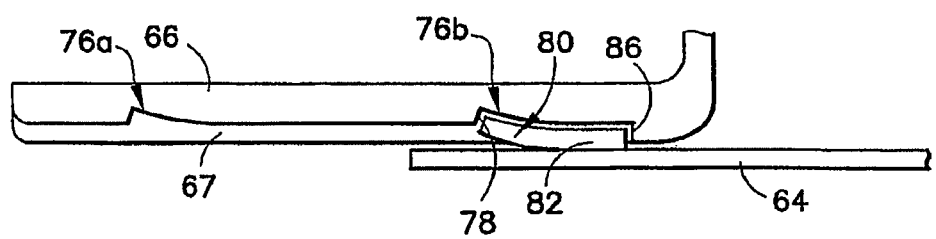
FIG. 7 is a side view illustrating the safety-shield system of the invention with the movable shield portion in the second position related to the holder shield portion.

With reference to FIGS. 5-7, interaction of the moveable shield portion 64 and guide rail 66 will now be described. A groove 67 is formed in the guide rail 66 and includes two spaced-apart first and second ramped notches 76a, 76b for receiving a flexible catch 80 formed on an inner surface of the moveable shield 64. Each first and second ramped notch 76a, 76b includes a substantially perpendicular back edge 78 and a curved front wall 79 relative to the direction of the movable shield portion 64. The flexible catch 80 has a fixed end 82 and a curved end 84. The curved end 84 is biased in the direction of the curved front edge 79 of the first and second ramped notches 76. The groove 67 also includes a stop surface 86 positioned at the front of the groove 67 relative to the needle cannula 12. The stop surface 86 functions to prevent the forward motion of the moveable shield portion 64 from beyond the extended second position.

FIG. 5 shows the relative position of the moveable shield portion 64 and the guide rail 66 when the movable shield portion 64 is in the first position. As shown, the flexible catch 80 has its curved end 84 positioned within first ramped notch 76a. As the movable shield portion 64 is moved to its second position the curved end 84 is bent out of first ramped notch 76a through interaction with the curved front edge 19 of the first ramped notch 76a such that the movable shield portion 64 can move in a direction along the length of the guide rail 66 as shown by arrow Y in FIG. 6. As the movable shield portion 64 reaches its second position, the flexible catch 80 interacts with stop surface 86 of the second ramped notch 76b which prevents continued forward motion of the movable shield portion 64 along the guide rail 66. At that second position, second ramped notch 76b provides clearance for the curved end 84 to expand. The substantially perpendicular back edge 78 of second ramped notch 76b functions as a reverse stop with the curved end 84 of the flexible catch 82 to prevent rearward movement of the movable shield portion 64 from its second position in a direction toward the first position.

Figure 3:
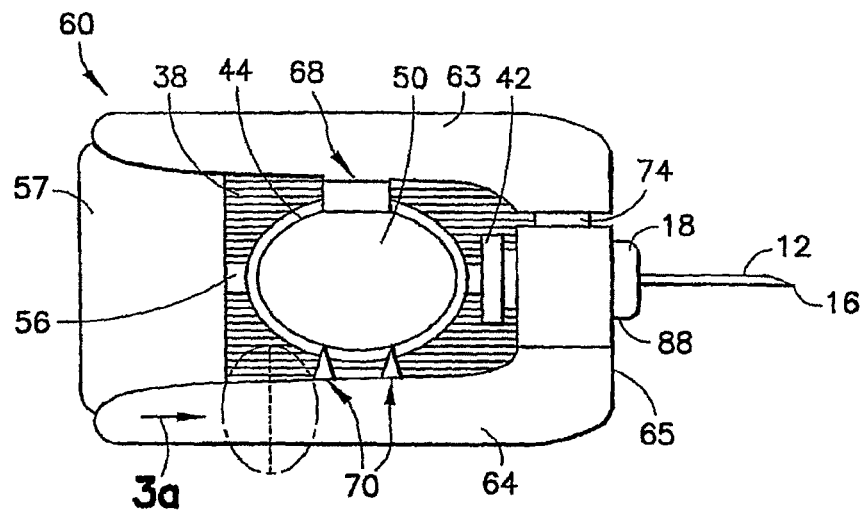
FIG. 3 shows a safety shield system of the invention engaging a compression syringe, with the movable shield portion in a first position related to the holder shield portion.
Figure 3A:
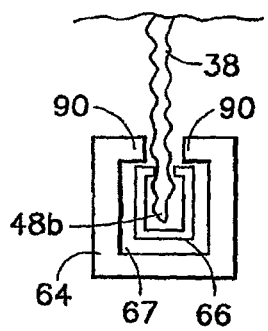
FIG. 3a shows a partial cross-sectional end view of the assembly of FIG. 3.
Figure 4:
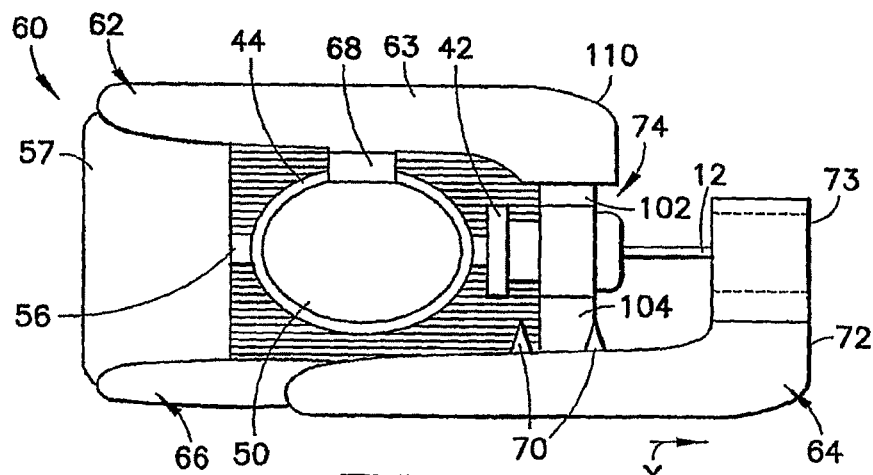
FIG. 4 shows the safety shield system of FIG. 3 with the movable shield portion in a second position related to the holder shield portion.
Figure 3B:
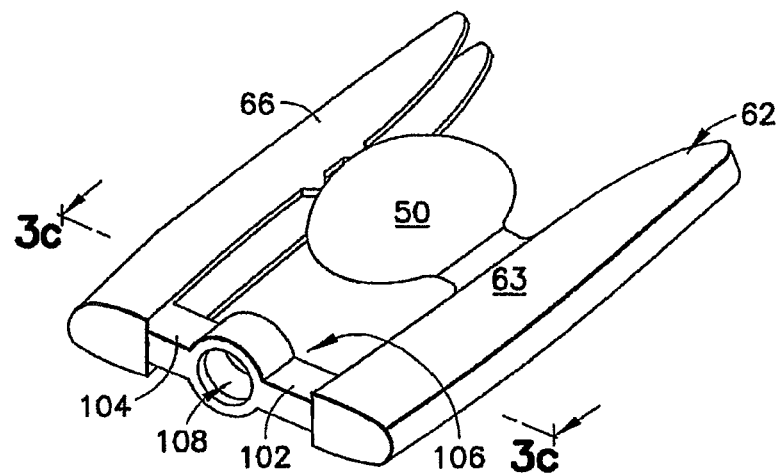
FIG. 3b is a perspective view of the movable shield portion of the needle shield system of FIG. 3.
Figure 3C:
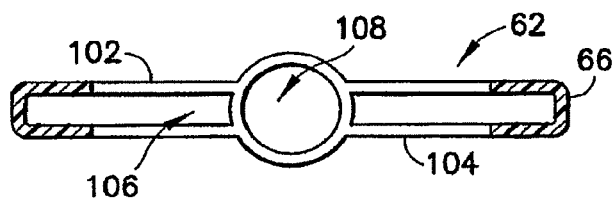
FIG. 3c is a cross view of the movable shield portion of FIG. 3a following the line A-A of FIG. 3.
Figure 3D:
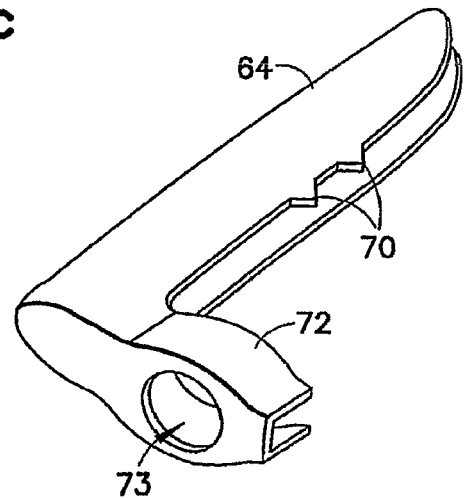
FIG. 3d is a perspective view of the holder shield portion of the needle shield system of FIG. 3.

In the depicted embodiment, the holder shield portion 62 is provided with a deflectable part such as a plate 50 connected to the holder shield portion by a flexible connection joint region 68 See FIGS. 3b and 4. The plate 50 has a shape complementary to the reservoir 46 and particularly its central region 40 and is located in regards to the central region 40. In an alternative not shown, the deflectable part can be connected to the movable shield portion.

To prevent premature movement of the movable shield portion 64 from the first position to the forward, second position wherein the tip 16 of the needle cannula 12 is covered, e.g., before medicament is administered, etc., a retaining means is provided. In accordance with an embodiment of the invention, the retaining means functions as an anchor and may be in the form of one or more frangible connection points 70 which extend from the moveable shield portion 64 to the holder shield portion 62 and, preferably, to the plate 50 covering the reservoir 46. It is contemplated that the safety shield system 60 is preferably made of molded plastic and that the connection points 70 are integrally molded with the moveable shield portion 64. With the moveable shield portion 64 in its first position as shown in FIG. 3, the application of heat to the connection points will cause the connection points to slightly melt and, upon cooling, adhere to the plate 50.

The connection points 70 may be in the form of thin ribs of plastic material that become detached from the holder shield portion during' regular use of the compression syringe 10, i.e., by compression of the plate 50 to expel the product from the reservoir 46 and to allow the movable shield portion 64 to be moved to its second position when the injection device is withdrawn from the injection site, as more fully described below.

The embodiment of the safety shield system 60 depicted in FIGS. 3, 3a and 4 relies either on an additional movement from the user to displace the movable shield portion 64 or on gravity to deploy the moveable shield portion 64 from its first position to its extended second position. As will be appreciated, for this to be accomplished and particularly for the gravity deployment, it is contemplated that minimal friction exists between the guide rail 66 and the movable shield portion 64 to allow the movable shield portion 64 to move to its extended second position under the force of its own weight. For this embodiment, the compression syringe 10 with the safety shield system 60 is preferably used to inject a patient with the compression syringe 10 oriented such that the tip 16 is angled or perpendicular to the ground. Thus, when the movable shield portion 64 is deployed by way of detachment of the frangible connection points 70 from the plate 50, the movable shield portion 64 can slide to its extended second position automatically, i.e., by gravity. Otherwise, the health care professional or user of the compression syringe 10 will, upon withdrawal of the sharp pointed end 16 from the patient, then orient the compression syringe 10 such that the tip 16 is pointed downward to allow the movable shield portion 64 to slide to its extended second position.

Figure 8:
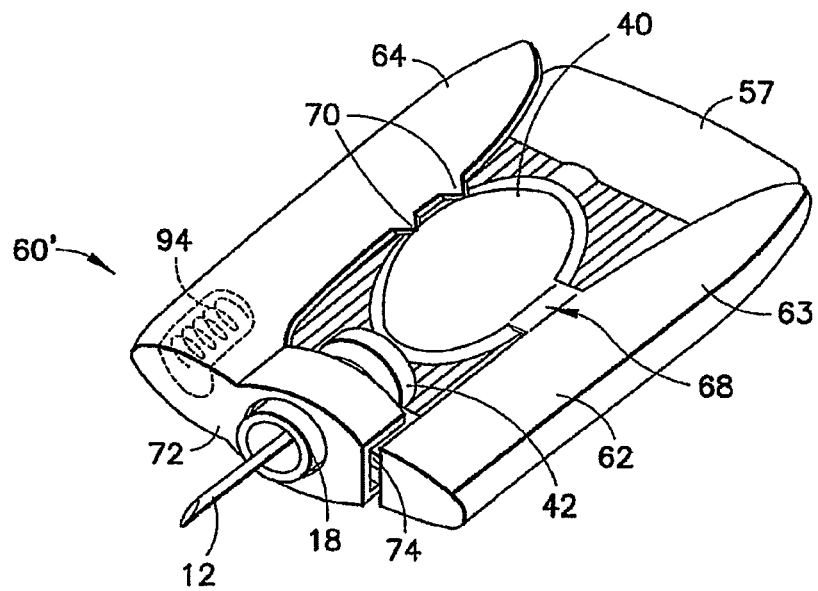
FIG. 8 shows a safety shield system according to another embodiment of the present invention, the safety shield system engaging a compression syringe and with the movable shield portion in the first position related to the holder shield portion.
Figure 9:
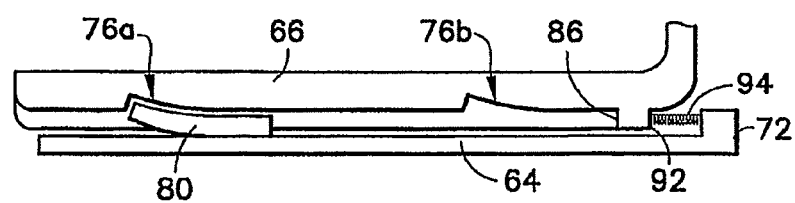
FIG. 9 is a side view illustrating the safety shield system of FIG. 8 with the movable shield portion in the first position related to the holder shield portion.

Instead of using gravity to deploy the moveable shield portion 64 from its first position to its extended second position wherein it is locked in place over the tip 16 of the needle cannula 12, an urging member 94 may be employed. Such an embodiment is depicted in FIGS. 8-11 wherein the urging member is depicted as a coil spring 94. Alternatively, a leaf spring may be used. As shown in FIGS. 8 and 9, the urging member 94 is positioned between an inner surface of the front face 72 of the moveable shield portion 64 and a leading edge surface 92 of the holder shield portion 62. It should be readily appreciated, however, that the spring 94 can be situated in other locations provided that it applies force between the moveable shield portion 64 and the compression syringe 10 to urge the moveable shield portion 64 to the extended second position. As shown in FIGS. 8 and 9, the spring 94 is compressed when the moveable shield portion 64 is in its first position whereby the retaining means, e.g., the frangible connection points 70 of the movable shield portion 64 remain attached to the holder shield portion 62, i.e. to the plate 50. Upon use of the compression syringe 10 wherein the plate 50 is compressed to administer medicament, the frangible connection points 70 will detach thereby allowing the spring 94 to expand to urge the moveable shield portion 64 to its extended second position.

Having now described the various features and components of the safety shield system 60 a description of an exemplary usage of the compression syringe will now be provided with reference to FIGS. 1-7. It should be understood by a person of ordinary skill in the art that the following description is provided as an illustrative and non-limiting example. A health care professional receives the compression syringe 10 with the safety shield system 60 attached thereto and with a desired single dosage of a medicament. Immediately prior to use, the protector cap 30 is pushed back against the needle hub 20, such as by grasping the external rim 36, to cause the back end 14 of the needle cannula 12 to puncture the nozzle membrane 22, thereby connecting the needle cannula to the reservoir 46. At this point, the moveable shield portion 64 is in its first position shown in FIGS. 3 and 5. The health care professional then removes the protector cap 30 and pierces the patient's skin with the forward tip 16 of the needle cannula 12. Thereafter, the plate 50 is compressed to cause medicament to be expelled from the reservoir 46 through the needle cannula 12 and into the patient. As the plate 50 deflects, the frangible connection points 70 break, thereby detaching the moveable shield portion 64 from the reservoir 46. When the medicament is expelled from the reservoir 46 so that the dose has been administered to a patient, the needle cannula tip 16 is removed from the patient. If the compression syringe 10 is positioned such that the needle cannula tip 16 is oriented toward the ground, then upon disconnection of the frangible connection points 70 from the plate 50, the moveable shield portion 64 will begin to move toward its second position. In other words, the flexible catch 80 will move from ramped notch 76a toward ramped notch 76b under the force of gravity and the forward motion of the moveable shield portion 64 will stop upon contact with the patient's skin. Thereafter, when the needle cannula 12 is removed from the patient, sufficient clearance is now provided for the moveable shield portion 64 to continue toward its extended second position in the direction shown by the arrow Y in FIG. 4 such that the flexible catch 80 will become secured within second ramped notch 76b. If, on the other hand, the injection is given to a patient wherein the compression syringe 10 is not oriented in a direction where the needle cannula tip 16 is facing the ground, then upon removal of the needle cannula 12 by the health care professional, the compression syringe 10 will then be oriented downward such that the movable shield portion 64 will slide to its extended second position under the force of gravity. The user can also push the movable shield portion 64 toward its second position with one finger. Once the movable shield portion 64 is in its extended second position, the compression syringe 10 can simply be discarded in any known manner typically used for syringe disposal.

If the urging member 94 is employed in the safety shield system 60 as shown in FIGS. 8-10, the orientation of the compression syringe 10 is irrelevant for deployment of the movable shield portion 64. Thus, once the connection points 70 are broken, the urging member 94 will begin moving the movable shield portion 64 until the front portion 72 of the movable shield portion 64 contacts the patient's skin. When the needle cannula tip 16 is removed from the patient, the urging member 94 will continue to move the movable shield portion 64 to its second position wherein it will lock in place such that the tip 16 of the needle cannula 12 will be shielded as shown in FIG. 10.

It should be appreciated that unlike the compression syringe disclosed in U.S. Pat. No. 4,955,871, the central portion 40 of the compression syringe 10 in accordance with an embodiment of the present invention does not need to remain compressed to prevent re-use of the compression syringe 10. This is because the deployment of the movable shield portion 64 to its extended second position will, by itself, render the compression syringe 10 unusable.

Figure 12:
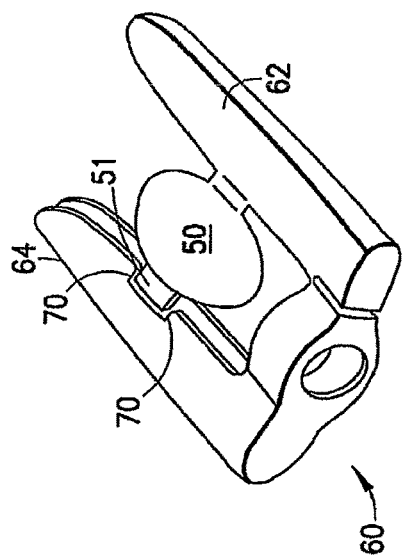

The safety shield system 60 of FIG. 12 is roughly similar to the one previously described according to FIGS. 1 to 11. The main difference relies on the retaining means which in this example comprise a tongue 51 connected to the plate 50 of the holder shield portion 62 and abutting with two stop walls 70 provided on the movable shield portion 64. As for the previous-example, upon use of the compression syringe (not shown on FIG. 12), wherein the plate 50 is compressed to administer medicament, the tongue 51 will disengage the stop walls 70 to allow the displacement of the movable shield portion 64 toward its extended second position.

Figure 13:
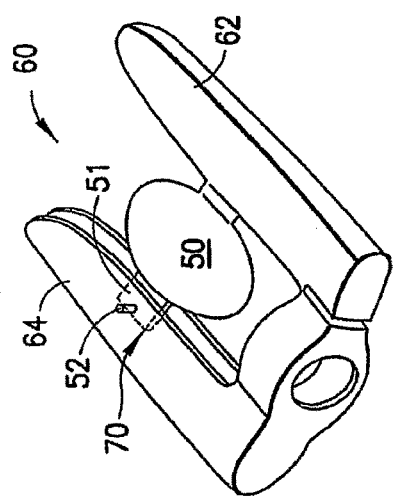
FIGS. 12, 13 and 15 are perspective views of alternate embodiments of the safety shield of the invention.

FIG. 13 shows another alternative where retaining means comprise a pin 52 connected to the tongue 51 of the plate 50 Of the holder shield portion 62 and received in a hole 70 provided on the movable shield portion 64. As for the previous example, upon use of the compression syringe (not shown on FIG. 13), wherein the plate 50 is compressed to administer medicament, the pin 52 will disengage the hole 70 to allow the displacement of the movable shield portion 64 toward its extended second position.

Figure 14:
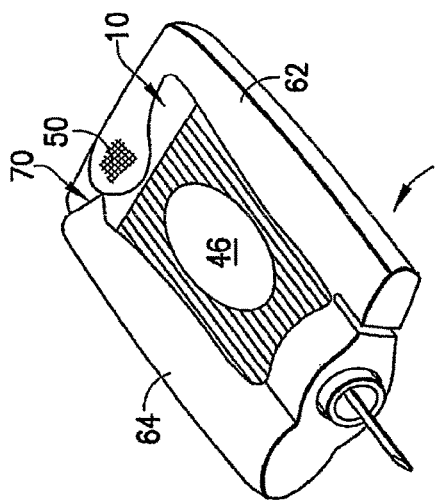
FIG. 14 is a perspective view of an alternate embodiment of the safety shield system and the compression syringe of the invention.

In the example shown on FIG. 14 the retaining means comprise a plate 50 connected to the holder shield portion 62 but which is not located above the reservoir 46 of the compression syringe 10. The plate 50 is connected by a frangible connection point 70 to movable shield portion 64. After having compressed the reservoir to inject the medicament, the user will move his fingers and press the plate 50 to detach the frangible connection point 70, allowing the spring 94 to expand (or gravity or a user of the compression syringe 10) to urge the movable shield portion 64 to its extended second position.

Figure 15:
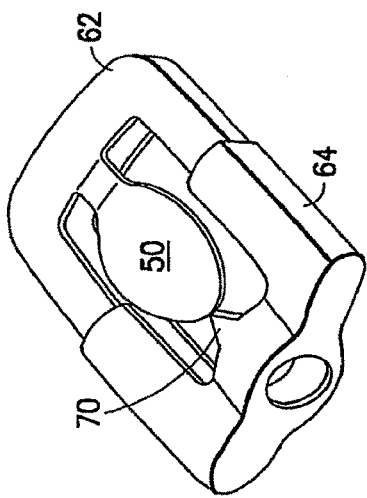

The safety shield system 60 of FIG. 15 is roughly similar to the one described according to FIGS. 1 to 11. In this example both movable shield portion and holder shield portion have a "U" shape oriented in opposite direction to enclose the compression syringe (not shown on FIG. 15). Retaining means are similar to those of example illustrated by FIGS. 1 to 11, that is to say a frangible connection point 70 located between the movable shield portion 64 and the plate 50 of the holder shield portion 62.

Figure 16:
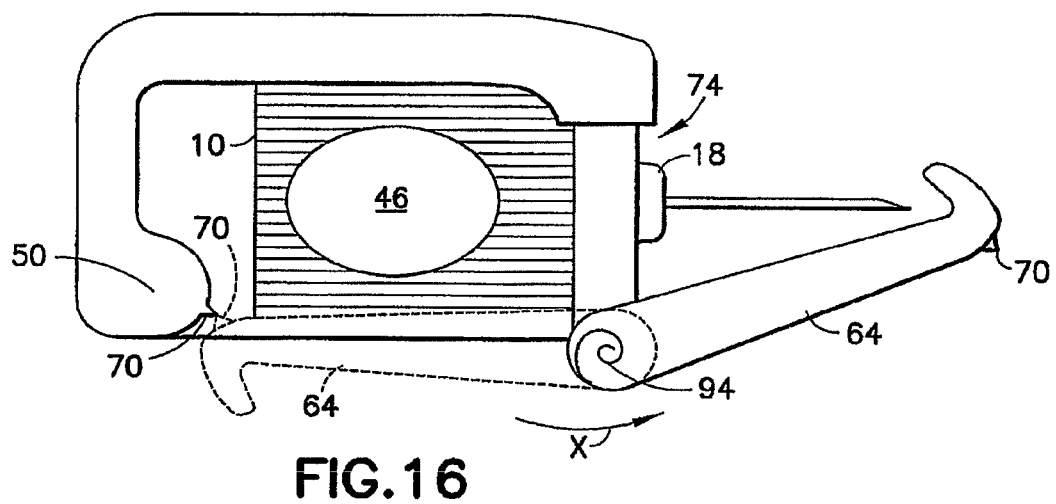
FIG. 16 is a perspective view of another alternate embodiment of the safety shield system and the compression syringe of the invention.

According to another alternate embodiment of the invention as shown in FIG. 16, the movable shield portion 64 can have a displacement movement from its first to its second positions different from a translation. For example, the movable shield portion 64 may comprise a pivoting protecting arm which is attached by one or more connection points 70 to a release plate 50. After a user compresses the reservoir 46 to dispense the medicament contained therein, the user will compress the plate 50 which will cause the connection points 70 to break and allow the movable shield portion 64 to pivot in the direction indicated by arrow "X" from the position shown by the dashed lines, to the position covering the tip of the needle cannula. The movement can be performed manually by the user grasping the movable shield 64 and rotating it to its extended position over the needle cannula tip. Preferably, an urging member such as a leaf spring 94 is provided, in a manner well known to those of ordinary skill in the art, to automatically pivot the movable shield 64 to the extended position once the connection points are broken. Thus, while there have shown and described and pointed out fundamental novel features of the invention as applied to a preferred embodiment thereof and described alternate embodiments, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A safety shield system for a compression syringe having a compressible reservoir, a needle cannula for fluid communication with the reservoir and having a forward tip, the safety shield system comprising:
   a holder shield portion designed to be attached to said compression syringe;
   a movable shield portion, designed to be movable relative to said compression syringe from a first position wherein the tip is exposed, to a second position wherein said movable shield portion covers said tip;
   said holder shield portion and movable shield portion being provided with one or more retaining elements arranged to cooperate in said first position to prevent said movable shield portion from moving toward its second position;
   wherein a part of said one or more retaining elements is provided on a deflectable part connected to at least one of said holder shield portion or movable shield portion, said deflectable part being manually deflectable to directly compress the reservoir to expel a product out of the compression syringe, wherein manual deflection of said deflectable part further acts to disengage said one or more retaining elements and allow said movable shield portion to be moved toward its second position.

2. The safety shield system of claim 1, wherein said movable shield portion is connected with said holder shield portion by a sliding connection allowing said movable shield portion to translate relating to said holder shield portion between said first and second positions.

3. The safety shield system of claim 2, wherein one of said holder shield portion and said movable shield portion has at least one guide rail or a sliding part complementary to said guide rail, said guide rail and said sliding part defining said sliding connection.

4. The safety shield system of claim 1, wherein said movable shield portion is connected with said holder shield portion by a pivoting connection allowing said movable shield portion to pivot relating to said holder shield portion between said first and second positions.

5. The safety shield system of claim 1, wherein said each of said movable shield portion and holder shield portion comprises at least one abutment surface.

6. The safety shield system of claim 3, wherein said movable shield portion and the holder shield portion are connected to each other by at least one frangible rib arranged to break upon compression of the deflectable part in a direction of the reservoir, said at least one frangible rib defining said one or more retaining elements.

7. The safety shield system of claim 1, wherein at least part of said deflectable part is engageable with said reservoir when said safety shield system is assembled with a compression syringe in order to be able to, when said deflectable part is manually deflected, squeeze said reservoir to expel said product out of said compression syringe.

8. The safety shield system of claim 2, wherein said sliding connection or a pivoting connection are arranged in order to limit friction between said movable shield portion and holder shield portion, to enable the free displacement of said movable shield portion toward the second position upon orienting a sharp pointed end toward the ground.

9. The safety shield system of claim 1, further comprising a locking element arranged to lock said movable shield portion in said second position.

10. The safety shield system of claim 6, wherein one of said holder shield portion and movable shield portion contains at least a first ramped notch and the other contains at least a first flexible catch arranged to be locked in said first ramped notch when said movable shield portion is in said first position to prevent said movable shield portion from moving from said first position.

11. The safety shield system of claim 9, wherein one of said holder shield portion and movable shield portion contains at least a first ramped notch and a second ramped notch arranged to lock a catch when said movable shield portion is in said second position to prevent said movable shield portion from moving from said second to first ramped notch, said second notch and catch defining part of said locking element.

12. The safety shield system of claim 1, further comprising an urging member positioned between said movable shield portion and said holder shield portion to urge said movable shield portion toward said second position.

13. The safety shield system of claim 9, wherein said urging member is a spring.

14. The safety shield system of claim 1, wherein the front portion of the movable shield portion defines an aperture through which the needle cannula extends when the safety shield system is assembled with a compression syringe and the movable shield portion is in the first position.

15. The safety shield system of claim 14, wherein said movable shield portion defines a L shape, the small branch of said L shape comprising said aperture and the long branch of said L shape defining part of a connecting element.

16. The safety shield system of claim 1, wherein said holder shield portion is provided with at least one gripping surface designed to be held by the user during operation of the safety shield system and/or of the compression syringe.

17. The safety shield system of claim 1, wherein the front portion of the holder shield portion defines a port designed to receive a needle hub when said safety shield system is assembled with a compression syringe.

18. The safety shield system of claim 16, wherein said holder shield portion has a U shape, one branch of said U shape defining a gripping surface, the other branch defining at least part of said connecting element, a basis of said U shape being formed by wings extending away from said port in opposite directions to said gripping surface and a connecting element.

19. The safety shield system of claim 15, wherein the front portion of the holder shield portion is configured to receive a portion of the basis of said overall "U" shape when the movable shield portion is in the first position.

20. The safety shield system of claim 10, wherein each of the first and second ramped notches consists of a substantially perpendicular back edge relative to the travel direction of the movable shield portion toward its second position, and a curved front wall, the curved front wall of the second one of the ramped notches causing movement of the catch out of the second one of the notches as the catch is moved from the second one of the notches to the first one of the notches.

21. The safety shield system of claim 20, wherein said second ramped notches is coupled with at least one stop surface arranged to prevent said catch to move past said second position, said stop surface and catch defining part of said locking.

* * * * *